(12) United States Patent
Duran et al.

(10) Patent No.: US 7,785,363 B2
(45) Date of Patent: Aug. 31, 2010

(54) SKEWED NODAL-FIBRIL EPTFE STRUCTURE

(75) Inventors: Julio Duran, Mt. Arlington, NJ (US); Krzysztof Sowinski, Looz (PL); Jamie S. Henderson, Oakland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 214 days.

(21) Appl. No.: 11/893,346

(22) Filed: Aug. 15, 2007

(65) Prior Publication Data

US 2009/0048658 A1 Feb. 19, 2009

(51) Int. Cl.
- *A61F 2/06* (2006.01)
- *A61B 19/00* (2006.01)
- *B32B 27/08* (2006.01)
- *B60R 21/16* (2006.01)
- *B31B 45/00* (2006.01)
- *B65D 39/00* (2006.01)
- *B29C 47/00* (2006.01)
- *B65D 1/02* (2006.01)
- *F16L 11/04* (2006.01)
- *D21H 11/00* (2006.01)
- *D01D 5/24* (2006.01)

(52) U.S. Cl. ............... 623/1.15; 128/898; 623/1.1; 623/1.13; 623/1.44; 623/1.54; 623/901; 428/34.1; 428/35.7; 428/36.1; 428/36.5; 428/36.9; 428/36.91; 428/36.92; 428/311.51; 264/209.1; 264/209.2

(58) Field of Classification Search ......... 623/1.1–1.54, 623/1.15
See application file for complete search history.

(56) References Cited

U.S. PATENT DOCUMENTS

| | | | |
|---|---|---|---|
| 4,225,547 A * | 9/1980 | Okita | 264/127 |
| 4,503,569 A | 3/1985 | Dotter | |
| 4,580,568 A | 4/1986 | Gianturco | |
| 4,732,152 A | 3/1988 | Wallsten et al. | |
| 4,733,665 A | 3/1988 | Palmaz | |
| 4,743,480 A * | 5/1988 | Campbell et al. | 428/36.5 |
| 4,856,516 A | 8/1989 | Hillstead | |
| 4,886,062 A | 12/1989 | Wiktor | |
| 5,437,900 A * | 8/1995 | Kuzowski | 428/36.1 |
| 5,628,782 A * | 5/1997 | Myers et al. | 623/2.25 |
| 5,814,405 A * | 9/1998 | Branca et al. | 428/311.51 |
| 5,874,032 A * | 2/1999 | Zdrahala et al. | 264/127 |
| 6,187,054 B1 * | 2/2001 | Colone et al. | 128/898 |
| 6,652,570 B2 * | 11/2003 | Smith et al. | 623/1.13 |
| 6,716,239 B2 * | 4/2004 | Sowinski et al. | 623/1.13 |
| 6,719,784 B2 * | 4/2004 | Henderson | 623/1.44 |
| 6,827,731 B2 * | 12/2004 | Armstrong et al. | 623/1.12 |
| 2002/0035396 A1 | 3/2002 | Heath | |
| 2006/0155371 A1 * | 7/2006 | Henderson | 623/1.49 |

* cited by examiner

*Primary Examiner*—David Isabella
*Assistant Examiner*—Jacqueline Woznicki
(74) *Attorney, Agent, or Firm*—Vidas, Arrett & Steinkraus (57) ABSTRACT

The ePTFE structure includes an ePTFE tubular structure having opposite ends and a longitudinal axis. The ePTFE tubular structure is formed from rotating the opposite ends relative to one another in a direction of rotation about the longitudinal axis. The ePTFE tubular structure has a node and fibril micro-structure in which substantially all of the fibrils are oriented in the direction of rotation.

20 Claims, 3 Drawing Sheets

SKEWED NODAL-FIBRIL EPTFE STRUCTURE

FIELD OF THE INVENTION

The present invention relates generally to structures containing expanded polytetrafluoroethylene (ePTFE) and methods for making the same. More specifically, the present invention relates to ePTFE tubular structures having a node and fibril micro-structure in which the fibrils have a specific orientation and methods for making such ePTFE tubular structures.

BACKGROUND OF THE INVENTION

It is well known to use extruded tubes of ePTFE as implantable intraluminal prostheses, particularly as grafts for vascular, esophageal, ureteral and enteral applications. ePTFE is particularly suitable as an implantable prosthesis as it exhibits superior biocompatibility. ePTFE tubes may be used as vascular grafts in the replacement or repair of a blood vessel as ePTFE exhibits low thrombogenicity. In vascular applications, the grafts are manufactured from ePTFE tubes which have a microporous micro-structure. This micro-structure allows natural tissue ingrowth and cell endothelization once implanted in the vascular system. This contributes to long term healing and patency of the graft. Vascular grafts formed of ePTFE have a fibrous state which is defined by the interspaced nodes interconnected by elongated fibrils.

One disadvantage of current thin-walled or thicker-walled implantable ePTFE tubes is their tendency to kink when subjected to bending forces or concentrated external radial forces. Kinking and luminal constriction can occur during or subsequent to implantation. Such kinking is normally undesirable and poses a risk to the patient.

Accordingly, in applications where kinking is likely, vascular grafts often have an additional support structure to prevent kinking. In some instances, external support structures, such as helical coils, are bonded around the outer surface of the ePTFE tube. Alternatively, individual rings may be bonded to the outer surface of the ePTFE by injection molding.

Such additional support structures have several disadvantages. For example, when the additional support structures are bonded to the outer surface of the ePTFE tube, they increase the outer diameter of the graft in the regions of the support structures. As a result, endoluminal implantation of the graft can be more difficult, such as, for example, when tunneling through tissue is required to implant the graft.

Another disadvantage of grafts having added support structures is that they are often made from materials which are different from the material of the graft wall and require added processing steps such as heat bonding or additional materials such as adhesive to adhere the support structure to the graft. Differential shrinkage or expansion of the external support structure relative to the ePTFE tube can cause the bond to weaken and/or the graft to twist significantly. Separation of the support structure from the graft is obviously undesirable. Additionally, twisting will normally distort the printed linear guideline which typically runs the length of the ePTFE tube and is used by practitioners to determine proper graft disposition to prevent implantation in a twisted configuration. Such distortion may result in the normally longitudinally linear guideline becoming helical or some other non-linear shape prior to implantation of the vascular graft in the patient, thereby defeating the purpose of the guideline.

Other ePTFE grafts have included external polymeric ribs which provide radial support to the lumen, but increase the outer diameter and wall thickness of the graft.

Thus, there is a need for PTFE tubes which are kink resistant without added support structures such as coils or rings and which do not increase the tube outer diameter. There is a further need for methods for fabricating such PTFE tubes which are reasonably practical and not unduly complex.

SUMMARY OF THE INVENTION

The ePTFE structure of the present invention includes an ePTFE tubular structure having opposite ends and a longitudinal axis. The ePTFE tubular structure is formed from rotating the opposite ends relative to one another in a direction of rotation about the longitudinal axis. The ePTFE tubular structure has a node and fibril micro-structure in which substantially all of the fibrils are oriented in the direction of rotation.

The ePTFE structure provides an ePTFE tubular structure which has increased flexibility and an increased range of bending of the tubular structure without kinking thereof. The increased flexibility reduces the likelihood of the ePTFE structure becoming kinked during the passage thereof through the more torturous regions of the anatomy of a patient. The increased flexibility and resistance to kinking are provided without having to add support structures, such as coils or rings, to the ePTFE tubular structure. Further, these benefits are achieved without having to increase the outer diameter of the tubular structure. Accordingly, these characteristics of the ePTFE structure which affect the handling and implantation thereof in the body of a patient are preserved while increasing the flexibility and resistance to kinking of the ePTFE structure.

The method of the present invention includes providing an ePTFE tubular structure having a longitudinal axis and a node and fibril micro-structure. One end of the ePTFE tubular structure is fixed to obstruct rotation thereof about the longitudinal axis. The second end of the ePTFE tubular structure is rotated about the longitudinal axis to orient the fibrils of the node and fibril micro-structure in the direction of rotation.

The method provides a specific orientation of the fibrils which results in the increased flexibility and resistance to kinking of the ePTFE tubular structure. Further, the method is not unduly complex which significantly enhances the utility thereof.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
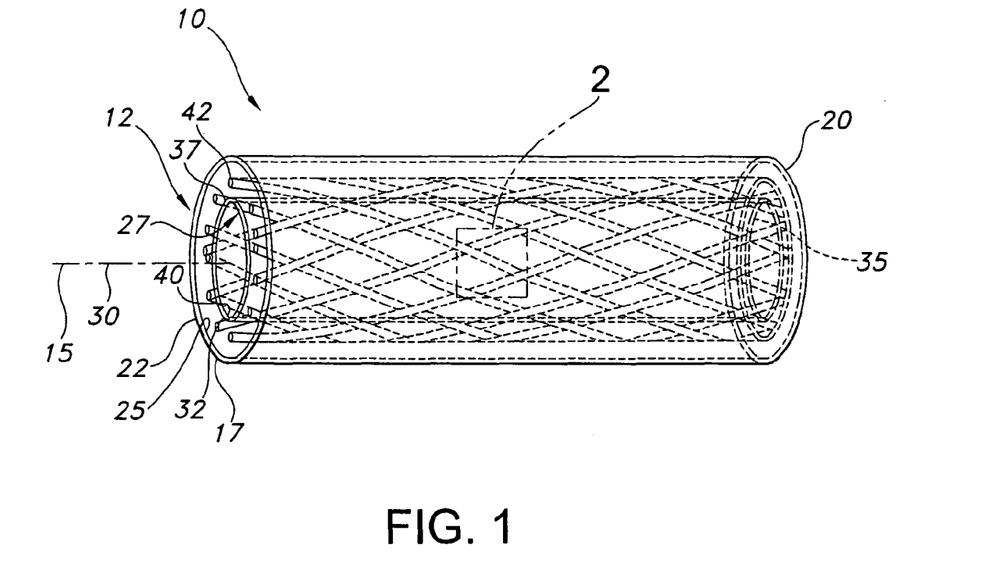
FIG. 1 is a perspective view, in schematic, of the skewed nodal-fibril ePTFE structure of the present invention, the ePTFE structure being shown as including cover and liner ePTFE tubular structures and a stent structure.

Referring to the drawings and more particularly to FIG. 1, a skewed nodal-fibril ePTFE structure 10 is shown for implantation within a body. The ePTFE structure 10 includes a cover ePTFE tubular structure 12 which has a longitudinal axis 15, and opposite ends 17, 20. The cover ePTFE tubular structure 12 has outer and inner surfaces 22, 25 and an annular or ring shaped cross-section. The ePTFE structure 10 further includes a liner ePTFE tubular structure 27 which has a longitudinal axis 30, and ends 32, 35. The liner ePTFE tubular structure 27 has outer and inner surfaces, 37, 40, and an annular or ring shaped cross-section.

The liner ePTFE tubular structure 27 is within the cover ePTFE tubular structure 12 in coaxial relation therewith such that the longitudinal axes 15, 30 coincide with one another. The longitudinal relation between the cover and the liner ePTFE tubular structures 12, 27 provide for the ends 17, 32 to have the same longitudinal positions and for the ends 20, 35 to have the same longitudinal positions relative to the longitudinal axis 15, 30.

The ePTFE structure 10 includes a stent structure 42 located between the cover and liner ePTFE tubular structures 12, 27, as shown in FIG. 1. The inner surface 25, stent structure 42, and outer surface 27 are secured to one another. This provides a composite structure in which the coaxial relation between the cover and liner ePTFE tubular structures 12, 27 is maintained and the coincident longitudinal positions of the end 17, 32, and ends 20, 35 are maintained.

The stent structure 42 may be formed of materials such as nitinol, elgiloy, stainless steel or cobalt chromium, including NP35N. Additionally, the stent structure 42 may be formed of materials such as stainless steel, platinum, gold, titanium and other biocompatible metals, as well as polymeric stents. Also, the stent structure 42 may be formed of materials including cobalt-based alloy such as elgiloy, platinum, gold, titanium, tantalum, niobium, and combinations thereof and other biocompatible materials, as well as polymers. Additionally, the stent structure 42 may include structural members which have an inner core formed of tantalum gold, platinum, iridium, or a combination thereof, and an outer cladding of nitinol to provide composite members for improved radio-opacity or visibility. Examples of such composite members are disclosed in U.S. Patent Application Publication 2002/0035396, the entire contents of which are hereby incorporated by reference herein.

The stent structure 42 may have various embodiments. For example, the stent structure 42 may be self-expanding or expandable by a balloon. The stent structure 42 may include one or more coiled stainless steel springs, helically wound coil springs including a heat-sensitive material, or expanding stainless steel stents formed of stainless steel wire in a zig-zag pattern. The stent structure 42 may be capable of radially contracting or expanding, such as by radial or circumferential distension or deformation. Self-expanding stents include stents which mechanically urge the stent to radially expand, and stents which expand at one or more specific temperatures as a result of the memory properties of the stent material for a specific configuration. Nitinol is a material which may be included in the stent structure 42 for providing radial expansion thereof both by mechanical urging, or by the memory properties of the nitinol based on one or more specific temperatures. The stent structure 42 may include one or more of the stents disclosed in U.S. Pat. Nos. 4,503,569, 4,733,665, 4,856,516, 4,580,568, 4,732,152, and 4,886,062, the entire contents of each of which are hereby incorporated by reference herein.

Figure 2:
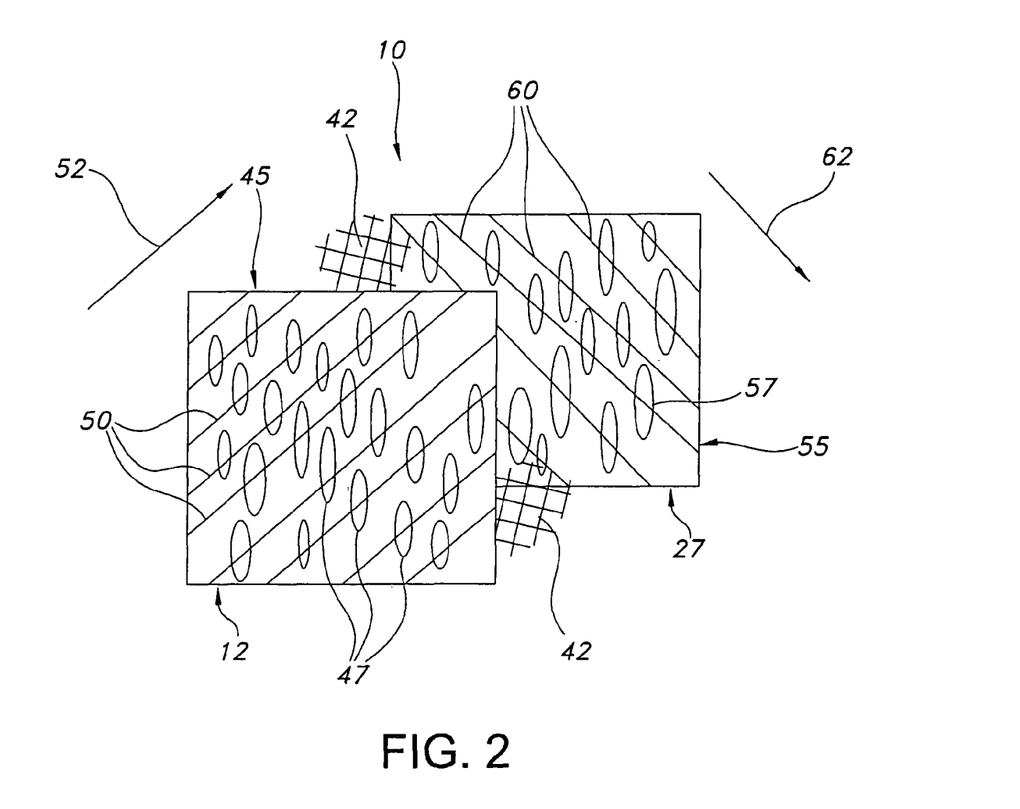
FIG. 2 is an enlarged exploded view, in schematic, of the section indicated by line 2 of FIG. 1 showing the respective node and fibril micro-structures of the cover and liner ePTFE tubular structures, portions of the stent structure being illustrated as broken away.

The cover ePTFE tubular structure 12 has a node and fibril micro-structure 45 which is defined by interspaced nodes 47 which are interconnected by elongated fibrils 50. The node and fibril micro-structure 45 is formed from rotating the ends 17, 20 relative to one another in a direction of rotation about the longitudinal axis 15. This results in substantially all of the fibrils 50 being oriented in a first direction of rotation 52 which corresponds to the direction of rotation of the ends 17, 20 relative to one another. Substantially all of the fibrils 50 have an inclined orientation relative to the longitudinal axis 15 such that the inclined orientation is substantially constant between the opposite ends 17, 20. The inclined orientation of the fibrils 50 provides the node and fibril micro-structure 45 with a helically positioned fibril micro-structure.

The cover ePTFE tubular structure 12 may have various embodiments in which different fractions of the fibrils 50 of the node and fibril micro-structure 45 are oriented in the first direction of rotation 52. In one embodiment of the cover ePTFE tubular structure 12, about 75% of the fibrils 50 of the node and fibril micro-structure 45 are oriented in the first oriented in the rotation 52. In an alternative embodiment of the cover ePTFE tubular structure 12, about 85% of the fibrils 50 of the node and fibril micro-structure 45 are oriented in the first direction of rotation 52. In a further alternative embodiment of the cover ePTFE tubular structure 12, about 95% of the fibrils 50 of the node and fibril micro-structure 45 are oriented in the first direction of rotation 52.

The nodes 47 of the node and fibril micro-structure 45 have a transverse orientation relative to the longitudinal axis 15, as shown in FIG. 2. The nodes 47 remain connected to corresponding fibrils 50 when the orientations thereof are changed. The orientations of the fibrils 50 are changed as a result of the rotation of the opposite ends 17, 20 of the cover ePTFE tubular structure 12 during the formation thereof. The connection of the nodes 47 to the corresponding fibrils 50 results in transverse displacement of the nodes 47 relative to the longitudinal axis 15 as a consequence of changes in the orientation of the fibrils.

The cover ePTFE tubular structure 12, including the node and fibril micro-structure 45, is sintered to lock the first direction of rotation 52 therein.

The liner ePTFE tubular structure 27 has a node and fibril micro-structure 55 which is defined by interspaced nodes 57 which are interconnected by elongated fibrils 60. The node and fibril micro-structure 55 is formed from rotating the ends 32, 35 relative to one another in a direction of rotation about the longitudinal axis 30. This results in substantially all of the fibrils 60 being oriented in a second direction of rotation 62 which corresponds to the direction of rotation of the ends 32, 35 relative to one another. Substantially all of the fibrils 60 have an inclined orientation relative to the longitudinal axis 30 such that the inclined orientation is substantially constant between the opposite ends 32, 35. The inclined orientation of the fibrils 60 provides the node and fibril micro-structure 55 with a helically positioned fibril micro-structure.

The liner ePTFE tubular structure 27 may have various embodiments in which different fractions of the fibrils 60 of the node and fibril micro-structure 55 are oriented in the second direction of rotation 62. In one embodiment of the liner ePTFE tubular structure 27, about 75% of the fibrils 60 of the node and fibril micro-structure 55 are oriented in the second direction of rotation 62. In an alternative embodiment of the liner ePTFE tubular structure 27, about 85% of the fibrils 60 of the node and fibril micro-structure 55 are oriented in the second direction of rotation 62. In a further alternative embodiment of the liner ePTFE tubular structure 27, about 95% of the fibrils 60 of the node and fibril micro-structure 55 are oriented in the second direction of rotation 62.

The nodes 57 of the node and fibril micro-structure 55 have a transverse orientation relative to the longitudinal axis 30, as shown in FIG. 2. The nodes 57 remain connected to corresponding fibrils 60 when the orientations thereof are changed. The orientations of the fibrils 60 are changed as a result of the rotation of the opposite ends 32, 35 of the liner ePTFE tubular structure 27 during the formation thereof. The connection of the nodes 57 to the corresponding fibrils 60 results in transverse displacement of the nodes 57 relative to the longitudinal axis 30 as a consequence of changes in the orientation of the fibrils 60.

The first direction of rotation 52 of the cover ePTFE tubular structure 12 is opposite to the second direction of rotation 62 of the liner ePTFE tubular structure 27, as shown in FIG. 2. In alternative embodiments, it is possible for the first and second directions of rotation 52, 62 to be different from one another without being in opposition. In still further alternative embodiments, it is possible for the first and second directions of rotations 52, 62 to be the same. Where the first and second directions of rotation 52, 62 are the same, bending of the associated cover and liner ePTFE tubular structures 12, 27 may produce a distinctive twisting thereof.

The liner ePTFE tubular structure 27, including the node and fibril micro-structure 55, is sintered to lock the second direction of rotation 62 therein.

Figure 3:
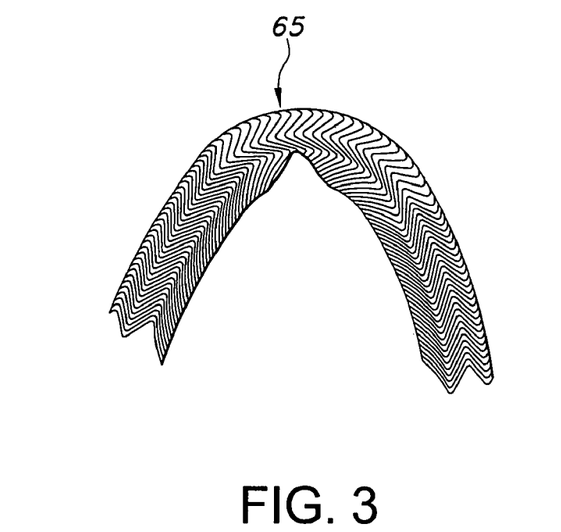
FIG. 3 is a photograph of an ePTFE structure showing the cover ePTFE tubular structure which has a node and fibril micro-structure having a standard straight orientation and not having the orientation of the present invention.
Figure 4:
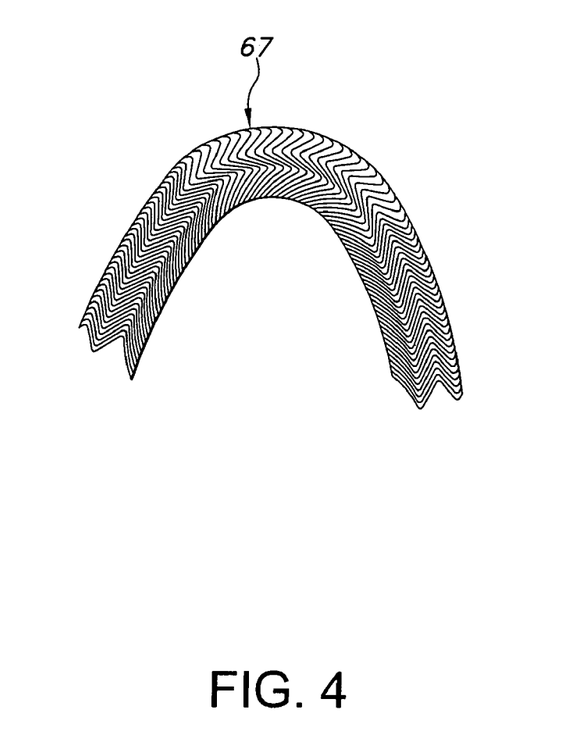
FIG. 4 is a photograph of an ePTFE structure showing the cover ePTFE tubular structure having a node and fibril micro-structure in which the fibrils are oriented according to the present invention.

The cover and liner ePTFE tubular structures 12, 27 provide increased flexibility and resistance to kinking as shown in FIGS. 3 and 4. FIG. 3 is a photograph of an ePTFE structure 65 which which has a cover ePTFE tubular structure, a stent structure located therein, and a liner ePTFE tubular structure located within the stent structure. The cover and liner ePTFE tubular structures of the ePTFE structure 65 have corresponding micro-structures which have standard straight orientations, or straight micro-structures. The cover and liner ePTFE tubular structures of the ePTFE structure 65 do not have the skewed node and fibril micro-structures 45, 55 of the cover and liner ePTFE tubular structures 12, 27. The ePTFE structure 65 is shown as being bent a sufficient degree to cause kinking thereof.

FIG. 4 is a photograph of an ePTFE structure 67 which has a cover ePTFE tubular structure, a stent structure located therein, and a liner ePTFE tubular structure located within the stent structure. The cover ePTFE tubular structure of the ePTFE structure 67 has a micro-structure which corresponds to the micro-structure 45 of the cover ePTFE tubular structure 12. The liner ePTFE tubular structure of the ePTFE structure 67 has a micro-structure which corresponds to the micro-structure 55 of the liner ePTFE tubular structure 27. The micro-structures of the cover and liner ePTFE tubular structure of the ePTFE structure 67 have respective directions of rotation which oppose one another. This opposition of the respective directions of rotation in the ePTFE structure 67 corresponds to the opposition of the first and second directions of rotation 52, 62 shown in FIG. 2.

The ePTFE structure 67 has been subjected to generally the same degree of bending as the ePTFE structure 65 shown in FIG. 3. The ePTFE structure 67 does not contain a kink in contrast to the ePTFE structure 65. FIGS. 3 and 4 illustrate how the ePTFE structure 67 may be bent through a higher angle of flex without developing a kink relative to the ePTFE structure 65. The improved flexibility and resistance to kinking of the ePTFE structure 67 relative to the ePTFE structure 65 results from the correspondences of the micro-structures of the cover and liner ePTFE tubular structures of the ePTFE structure 67 to the micro-structures 45, 55 of the cover and liner ePTFE tubular structures 12, 27.

The cover and liner ePTFE tubular structures 12, 27 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), anti-neoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

The cover and liner tubular structures 12, 27 are preferably formed of ePTFE. Alternatively, or in combination with ePTFE, the tubular structures 12, 27 may be formed of biocompatible materials, such as polymers which may include fillers such as metals, carbon fibers, glass fibers or ceramics. Such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the tubular structures 12, 27.

An alternative embodiment of the ePTFE structure 10 can include a single ePTFE tubular structure having a node and fibril micro-structure which is skewed, such as the node and fibril micro-structures 45, 55. Such a single ePTFE tubular structure may be included in a further alternative embodiment of the ePTFE structure 10 in which a stent structure, such as the stent structure 42, is located within the single ePTFE tubular structure or the single ePTFE tubular structure is located within the stent structure.

Figure 5:
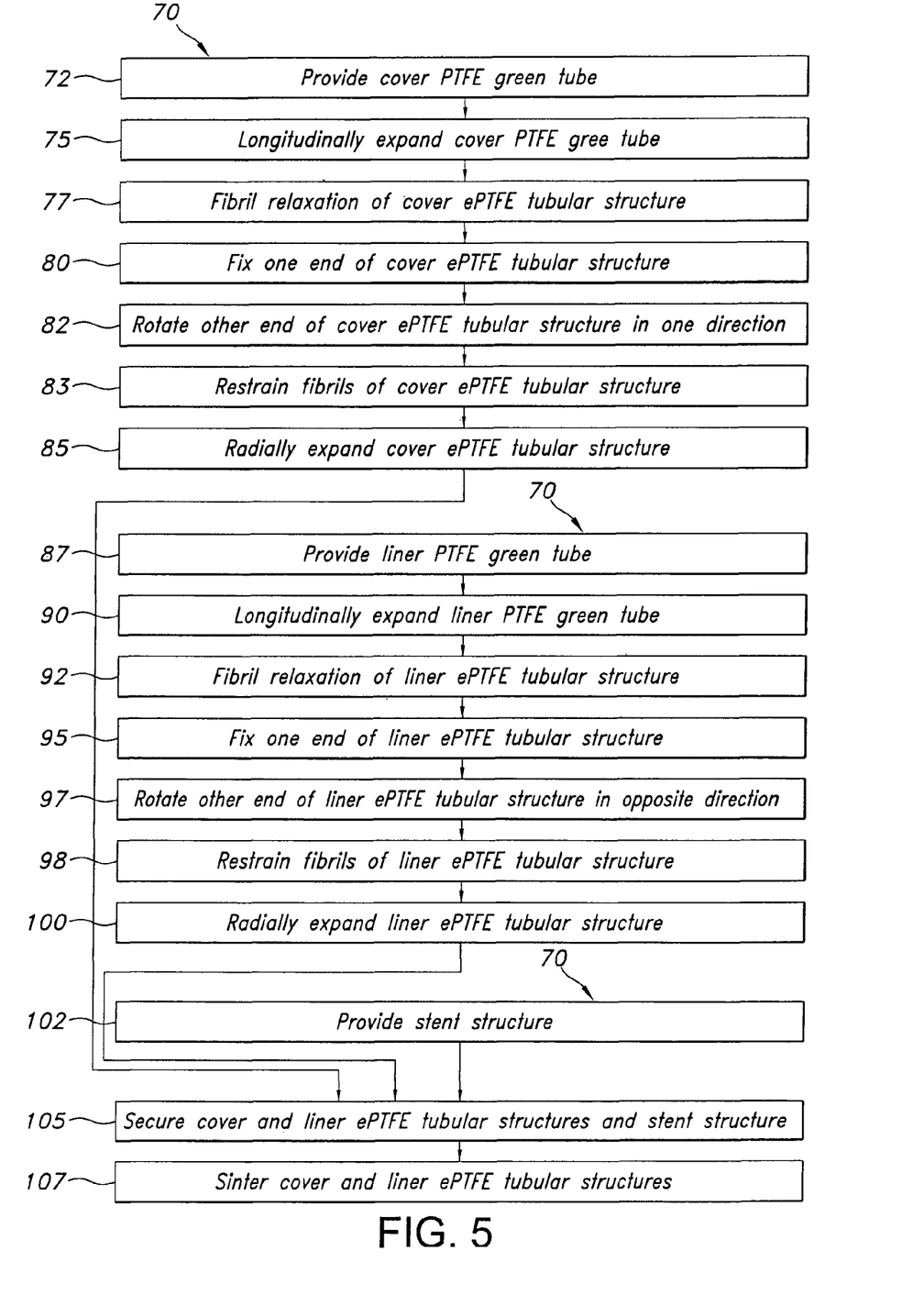
FIG. 5 is a block diagram showing a method for making a skewed nodal-fibril ePTFE structure of the present invention, the method being shown as including rotating one end of an ePTFE tubular structure relative to the other end thereof.

A method 70 for making the ePTFE structure 10 is represented by the block diagram of FIG. 5. The method 70 includes providing 72 a cover PTFE green tube. The method 70 further includes longitudinally expanding 75 the cover PTFE green tube to form the cover ePTFE tubular structure, such as the cover ePTFE tubular structure 12.

The method 70 further includes relaxing 77 the fibrils of the node and fibril micro-structure of the cover ePTFE tubular structure. The relaxing 77, which may be referred to as a fibril relaxation process, is performed by reducing or limiting the support of the cover ePTFE tubular structure, such as the structural support thereof, to allow expansion and contraction of the cover ePTFE tubular structure. The relaxation 77 further includes heating the cover ePTFE tubular structure such that a temperature thereof is maintained at about 300 to 600 degrees F. (Fahrenheit) for a duration of about 1 to 30 minutes.

Following the fibril relaxation 77, one end of the cover ePTFE tubular structure is fixed to obstruct rotation thereof about the longitudinal axis of the cover ePTFE tubular structure. An embodiment of the cover ePTFE tubular structure which may be fixed 80 is the cover ePTFE tubular structure 12. The end 17 of the cover ePTFE tubular structure 12 may be fixed 80 to obstruct rotation thereof about the longitudinal axis 15.

Following the fixing 80, the other end of the cover ePTFE tubular structure is rotated 82 about the longitudinal axis thereof to orient the fibrils of the node and fibril micro-structure in the direction of rotation of the other end relative to the one end of the cover ePTFE tubular structure. The other end of the cover ePTFE tubular structure may be rotated 82 up to about 720 degrees around the longitudinal axis relative to the one end of the cover ePTFE tubular structure. In alternative embodiments, the rotation 82 may exceed 720 degrees. An embodiment of the cover ePTFE tubular structure which may be rotated 82 is the cover ePTFE tubular structure 12. The end 20 of the cover ePTFE tubular structure 12 may be rotated about the longitudinal axis 15 to orient the fibrils 50 of the node and fibril micro-structure 45 in the first direction of rotation 52 which corresponds to the direction of rotation of the end 20 relative to the end 17 of the cover ePTFE tubular structure 12. The end 20 of the cover ePTFE tubular structure 12 may be rotated 82 up to about 720 degrees around the longitudinal axis 15 relative to the end 17 of the cover ePTFE tubular structure 12. In alternative embodiments, the rotation 82 may exceed 720 degrees.

The method 70 includes restraining 83 the fibrils of the node and fibril micro-structure from returning to a corresponding direction of rotation relative to the longitudinal axis before the completion of the rotation 82. The restraining 83 may be provided by fixing the end of the cover ePTFE tubular structure which was rotated 82 and continuing the fixation 80 of the opposite end of the cover ePTFE tubular structure. An embodiment of the restraint 83 is possible in which the end 20 of the cover ePTFE tubular structure 12 which was rotated 82 is fixed and the opposite end 17 which was fixed 80 during the rotation 82 is continued to be fixed.

The method 70 further includes radially expanding 85 the cover ePTFE tubular structure after the rotation 82.

The method 70 further includes providing 87 a liner PTFE green tube. The method 70 further includes longitudinally expanding 90 the liner PTFE green tube to form the liner ePTFE tubular structure, such as the liner ePTFE tubular structure 27.

The method 70 further includes relaxing 92 the fibrils of the node and fibril micro-structure of the liner ePTFE tubular structure. The relaxing 92, which may be referred to as a fibril relaxation process, is performed by reducing or limiting the support of the liner ePTFE tubular structure, such as the structural support thereof, to allow expansion and contraction of the liner ePTFE tubular structure. The relaxation 92 further includes heating the liner ePTFE tubular structure such that a temperature thereof is maintained at about 300 to 600 degrees F. for a duration of about 1 to 30 minutes.

Following the fibril relaxation 92, one end of the liner ePTFE tubular structure is fixed to obstruct rotation thereof about the longitudinal axis of the liner ePTFE tubular structure. An embodiment of the liner ePTFE tubular structure which may be fixed 95 is the liner ePTFE tubular structure 27. The end 32 of the liner ePTFE tubular structure 27 may be fixed 95 to obstruct rotation thereof about the longitudinal axis 30.

Following the fixing 95, the other end of the liner ePTFE tubular structure is rotated 97 about the longitudinal axis thereof to orient the fibrils of the node and fibril micro-structure in the direction of rotation of the other end relative to the one end of the liner ePTFE tubular structure. The other end of the liner ePTFE tubular structure may be rotated 97 up to about 720 degrees around the longitudinal axis relative to the one end of the liner ePTFE tubular structure. In alternative embodiments, the rotation 97 may exceed 720 degrees.

An embodiment of the liner ePTFE tubular structure which may be rotated 97 is the liner ePTFE tubular structure 27. The end 35 of the liner ePTFE tubular structure 27 may be rotated about the longitudinal axis 30 to orient the fibrils 60 of the node and fibril micro-structure 55 in the second direction of rotation 62 which corresponds to the direction of rotation of the end 35 relative to the end 32 of the liner ePTFE tubular structure 27. The end 35 of the liner ePTFE tubular structure 27 may be rotated 97 up to about 720 degrees around the longitudinal axis 30 relative to the end 32 of the liner ePTFE tubular structure 27. In alternative embodiments, the rotation 97 may exceed 720 degrees.

The method 70 includes restraining 98 the fibrils of the node and fibril micro-structure from returning to a corresponding direction of rotation relative to the longitudinal axis before the completion of the rotation 97. The restraining 98 may be provided by fixing the end of the liner ePTFE tubular structure which was rotated 97 and continuing the fixation 95 of the opposite end of the liner ePTFE tubular structure. An embodiment of the restraint 98 is possible in which the end 35 of the liner ePTFE tubular structure 27 which was rotated 97 is fixed and the opposite end 32 which was fixed 95 during the rotation 97 is continued to be fixed.

The method 70 further includes radially expanding 100 the liner ePTFE tubular structure after the rotation 97.

The processing of the liner ePTFE tubular structure, which includes the steps 87, 90, 92, 95, 97, 100, may be performed concurrently with, or before or after the processing of the cover ePTFE tubular structure, which includes the steps 72, 75, 77, 80, 82, 85.

The method 70 further includes providing 102 a stent structure, such as the stent structure 42. The stent structure is secured 105 to the cover and liner ePTFE tubular structures such that the liner ePTFE tubular structure is within the cover ePTFE tubular structure and in coaxial relation therewith. The securing 105 further provides for the stent structure to be located between the cover and liner ePTFE tubular structures.

An embodiment of the assembly which is provided by the securing 105 is shown in FIG. 1 which illustrates the liner ePTFE tubular structure 27 within the cover ePTFE tubular structure 12 in coaxial relation therewith. The stent structure 42 is located between the inner and outer surfaces 25, 37.

The securing 105 of the cover and liner ePTFE tubular structures and the stent structure is preferably provided by the stent structure having apertures to allow direct contact between the inner surface of the cover ePTFE tubular structure and the outer surface of the liner ePTFE tubular structure. Such direct contact enables the cover and liner ePTFE tubular structures to be laminated to one another through the apertures in the stent structure to provide the securing 105. The lamination secures 105 the cover and liner ePTFE tubular structures and stent structure to one another such that the structures are fixed to one another and relative displacement between them is obstructed. The apertures in the stent structures also provide for an alternative embodiment of the securing 105 which includes providing an adhesive material which is bonded to the inner surface of the cover ePTFE tubular structure and the outer surface of the liner ePTFE tubular structure through the apertures in the stent structure. This bonding of the adhesive material secures 105 the cover and liner tubular structures and the stent structure to one another such that the structures are fixed to one another and relative displacement between the structures is obstructed.

The cover and liner ePTFE tubular structures are arranged relative to one another such that the securing 105 thereof provides for the direction of rotation of the micro-structure of the cover ePTFE tubular structure, which constitutes a first direction of rotation, to be opposite to the direction of rotation of the micro-structure of the liner ePTFE tubular structure, which constitutes a second direction of rotation. An embodiment in which cover and liner ePTFE tubular structures are secured 105 to one another such that the first and second directions of rotation oppose one another is shown in FIG. 2. In this embodiment, the first direction of rotation 52 of the fibrils 50 of the cover ePTFE tubular structure 12 opposes the second direction of rotation 62 of the fibrils 60 of the liner ePTFE tubular structure 27. In an alternative embodiment, it is possible for the first and second directions of rotation to be different from one another without being in relative opposition. A further alternative embodiment is possible in which the first and second directions of rotation are the same. The relation between the first and second directions of rotation, such as the first and second directions of rotation 52, 62, may be controllably selected by performing the respective rotations 82, 97 to corresponding specific degrees.

The securing 105 of the cover and liner ePTFE tubular structures to one another provides resistance to the fibrils of the respective node and fibril micro-structures from returning to the orientations thereof relative to the longitudinal axis before the completion of the rotations 82, 97. This resistance is provided to the fibrils of the cover ePTFE tubular structure by the securing 105 of the liner ePTFE tubular structure thereto. Additionally, the resistance is provided to the fibrils of the liner ePTFE tubular structure by the securing 105 of the cover ePTFE tubular structure thereto. An embodiment of the resistance to the return of the fibrils to an orientation thereof before the rotation 82 is shown in FIG. 2 by the securing 105 of the inner and outer surfaces 25, 37. This attachment resists the return of the fibril 50 from the first direction of rotation 52 to an orientation thereof before the completion of the rotation 82, and resists the return of the fibrils 60 from the second direction of rotation 62 to an orientation thereof before the completion of the rotation 97.

The method 70 further includes sintering 107 the cover and liner ePTFE tubular structures. As shown in FIG. 5, the sintering 107 follows the securing 105. In an alternative embodiment of the method 70, it is possible for the cover and liner ePTFE tubular structures to be sintered 107 separately before the securing 105. Embodiments of the cover and liner ePTFE tubular structures 12, 27 which are formed from the sintering 107 are shown in FIG. 1. The sintering 107 may include heating the cover and liner ePTFE tubular structures such that a temperature thereof is maintained at about 630 to 700 degrees F. for a duration of about 1 to 60 minutes.

The method 70 further includes an alternative embodiment in which the rotations 82, 97 are performed on the cover and liner ePTFE tubular structures, respectively, after the liner ePTFE tubular structure is located within the cover ePTFE tubular structure in coaxial relation therewith. In this alternative embodiment of the method 70 in which the rotations 82, 97 are performed on the cover and liner ePTFE tubular structures which are in coaxial relation with one another, the rotations 82, 97 may be performed concurrently or at different times. This alternative embodiment of the method 70 in which the rotations 82, 97 are performed on the cover and liner ePTFE tubular structures which are in coaxial relation with one another may be carried out on the cover and liner ePTFE tubular structures, such as the cover and liner ePTFE tubular structures 12, 27 which have the coaxial relation shown in FIG. 1.

In a further alternative embodiment of the method 70, the radial expansions 85, 100 of the cover and liner ePTFE tubular structures, respectively, may be performed after the securing 105 of the cover and liner ePTFE tubular structures and stent structure. The radial expansions 85, 100 may be performed after the securing 105 of the cover and liner ePTFE tubular structures, such as the cover and liner ePTFE tubular structures 12, 27 shown in FIG. 1.

U.S. Pat. No. 6,716,239 is hereby incorporated by reference herein. The U.S. Patent Application filed in the U.S. Patent and Trademark Office on even date herewith and entitled "Preferentially Varying-Density ePTFE Structure", having as the inventors Julio Duran, Jamie S. Henderson, and Krzysztof Sowinski, and identified by the is hereby incorporated by reference herein.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An ePTFE structure comprising an ePTFE tubular structure having opposite ends and a longitudinal axis, said ePTFE tubular structure being formed by rotating said opposite ends relative to one another in a direction of rotation about said longitudinal axis, said ePTFE tubular structure comprising a node and fibril micro-structure, wherein the node and fibril micro-structure comprises nodes and fibrils, wherein each node comprises a longitudinal axis therethrough, in which substantially all of said fibrils are longitudinally oriented in said direction of rotation, wherein the direction of rotation is oblique to the longitudinal axis of said tubular structure, wherein the longitudinal axis of each nodes is perpendicular to the longitudinal axis of the tubular structure, and the fibrils are rotated relative to the nodes and the longitudinal axis.

2. An ePTFE structure according to claim 1, wherein about 75% of said fibrils of said node and fibril micro-structure are oriented in said direction of rotation.

3. An ePTFE structure according to claim 2, wherein about 85% of said fibrils of said node and fibril micro-structure are oriented in said direction of rotation.

4. An ePTFE structure according to claim 3, wherein about 95% of said fibrils of said node and fibril micro-structure are oriented in said direction of rotation.

5. An ePTFE structure according to claim 1, wherein said nodes of said node and fibril micro-structure have a transverse orientation relative to said longitudinal axis.

6. An ePTFE structure according to claim 1, wherein said ePTFE tubular structure constitutes a cover ePTFE tubular structure, said direction of rotation defining a first direction of rotation,
said ePTFE structure comprising a liner ePTFE tubular structure having opposite ends and a longitudinal axis, said liner ePTFE tubular structure being formed from rotating said opposite ends thereof relative to one another in a second direction of rotation about said longitudinal axis of said liner ePTFE tubular structure, said liner ePTFE tubular structure having a node and fibril micro-structure in which substantially all of said fibrils are oriented in said second direction of rotation,
said liner ePTFE tubular structure being secured to said cover ePTFE tubular structure such that said cover and liner ePTFE tubular structures are in coaxial relation to one another.

7. An ePTFE structure according to claim 6, wherein said first direction of rotation is opposite to said second direction of rotation.

8. An ePTFE structure according to claim 6, and further comprising a stent structure located between said cover and liner ePTFE tubular structures such that said stent structure is secured to said cover and liner ePTFE tubular structures.

9. An ePTFE structure comprising an ePTFE tubular structure having opposite ends located along a longitudinal axis, said ePTFE tubular structure comprising a node and fibril micro-structure, wherein the node and fibril micro-structure comprises nodes and fibrils, wherein the nodes each comprise a longitudinal axis therethrough, in which substantially all of said fibrils have an inclined orientation relative to said longitudinal axis of the tubular structure wherein said inclined orientation is substantially constant between said opposite ends, wherein the longitudinal axis of each nodes is perpendicular to the longitudinal axis of the tubular structure, and wherein substantially all the fibrils are at an oblique angle relative to the longitudinal axis and the nodes.

10. a method for making an ePTFE structure, said method comprising:
providing an ePTFE tubular structure having a longitudinal axis and opposite ends, the ePTFE tubular structure having a node and fibril micro-structure, wherein the node and fibril micro-structure comprises nodes and fibrils, fixing one end of the ePTFE tubular structure to obstruct rotation thereof about the longitudinal axis of the ePTFE tubular structure, rotating the other end of the ePTFE tubular structure about the longitudinal axis thereof to orient the fibrils of the node and fibril micro-structure in the direction of rotation of the other end relative to the one end of the ePTFE tubular structure; wherein the nodes of the node and fibril micro-structure each have a longitudinal axis therethrough, and wherein the longitudinal axis of each of the nodes are perpendicular to the longitudinal axis and the fibrils are at an oblique angle relative to the longitudinal axis and the nodes.

11. A method according to claim 10, wherein said rotating comprises rotating the other end of the ePTFE tubular structure up to about 720 degrees around the longitudinal axis relative to the one end of the ePTFE tubular structure.

12. A method according to claim 10, and further comprising relaxing the fibrils before said rotating and after extruding and providing.

13. A method according to claim 12, wherein said relaxing comprises limiting the support of the ePTFE tubular structure to allow expansion and contraction thereof,
said relaxing further comprising heating the ePTFE tubular structure such that a temperature thereof is maintained at about 300 to 600 degrees F. for a duration of about 1 to 30 minutes.

14. A method according to claim 10, wherein said extruding and providing comprises providing a PTFE green tube, said method further comprising longitudinally expanding the PTFE green tube to form the ePTFE tubular structure before said fixing thereof such that said fixing and rotating is of the ePTFE tubular structure which has been longitudinally expanded.

15. A method according to claim 10, and further comprising radially expanding the ePTFE tubular structure after said rotating.

16. A method according to claim 10, wherein the ePTFE tubular structure constitutes a cover ePTFE tubular structure,
said method further comprising providing a liner ePTFE tubular structure which has a longitudinal axis, the liner ePTFE tubular structure having a node and fibril micro-structure,
said method further comprising fixing one end of the liner ePTFE tubular structure to obstruct rotation thereof about the longitudinal axis of the liner ePTFE tubular structure,
said method further comprising rotating a second end of the liner ePTFE tubular structure about the longitudinal axis of the liner ePTFE tubular structure to orient the fibrils in the direction of rotation of the second end of the liner ePTFE tubular structure relative to the one end of the liner ePTFE tubular structure,
said method further comprising securing the cover and liner ePTFE tubular structures to one another such that the liner ePTFE tubular structure is within the cover ePTFE tubular structure in coaxial relation therewith.

17. A method according to claim 16, wherein said rotating of said cover ePTFE tubular structure provides the fibrils thereof with an orientation in the direction of rotation of the second end of the cover ePTFE tubular structure which constitutes a first direction of rotation,
said rotating of said liner ePTFE tubular structure provides the fibrils thereof with an orientation in the direction of rotation of the second end of the liner ePTFE tubular structure which constitutes a second direction of rotation such that said second direction of rotation is different from said first direction of rotation.

18. A method according to claim 17, wherein said rotating of said cover ePTFE tubular structure and said rotating of said liner ePTFE tubular structure provides for said first and second directions of rotation to oppose one another after said securing.

19. A method according to claim 17, wherein the ePTFE tubular structure constitutes a cover ePTFE tubular structure,
said method further comprising restraining the fibrils of the node and fibril micro-structure from returning to an orientation thereof relative to the longitudinal axis before a completion of said rotating, said method further comprising providing a liner ePTFE tubular structure, said method further comprising securing the cover and liner ePTFE tubular structures to one another such that the liner ePTFE tubular structure resists the fibrils from returning to an orientation thereof relative to the longitudinal axis of the cover ePTFE tubular structure before said completion of said rotating.

20. A method according to claim 16, and further comprising providing a stent structure before said securing, said securing further comprising securing the stent structure to the cover and liner ePTFE tubular structures such that the stent structure is between the cover and liner ePTFE tubular structures.

* * * * *